United States Patent [19]

Myers et al.

[11] Patent Number: 5,832,450
[45] Date of Patent: Nov. 3, 1998

[54] ELECTRONIC MEDICAL RECORD USING TEXT DATABASE

[75] Inventors: Dennis Lee Myers; Kim Steven Culp, both of Temple, Tex.

[73] Assignee: Scott & White Memorial Hospital, Temple, Tex.

[21] Appl. No.: 841,778

[22] Filed: May 5, 1997

Related U.S. Application Data

[63] Continuation of Ser. No. 354,446, filed as PCT/JP93/01676, Nov. 16, 1993, abandoned, which is a continuation of Ser. No. 84,282, Jun. 28, 1993, abandoned.

[51] Int. Cl.[6] .................................................. G06F 159/00
[52] U.S. Cl. ...................................................... 705/3; 705/1
[58] Field of Search ................................ 705/1–4; 707/1, 707/10, 100, 102, 104, 200, 537

[56] References Cited

U.S. PATENT DOCUMENTS

| | | | |
|---|---|---|---|
| 4,857,716 | 8/1989 | Gombrich et al. | 235/462 |
| 5,054,096 | 10/1991 | Beizer | 382/41 |
| 5,065,315 | 11/1991 | Garcia | 364/413.01 |
| 5,072,383 | 12/1991 | Brimm et al. | 364/413.02 |
| 5,155,726 | 10/1992 | Spinney et al. | 370/85.5 |
| 5,185,860 | 2/1993 | Wu | 395/200 |
| 5,247,437 | 9/1993 | Vale et al. | 364/419.19 |
| 5,247,611 | 9/1993 | Norden-Paul et al. | 395/161 |
| 5,265,010 | 11/1993 | Evans-Pagnelli et al. | 364/413.02 |
| 5,319,543 | 6/1994 | Wilhelm | 364/401 M |
| 5,361,202 | 11/1994 | Doue | 364/413.01 |
| 5,473,537 | 12/1995 | Glazer et al. | 364/419.2 |

*Primary Examiner*—Frantzy Poinvil
*Attorney, Agent, or Firm*—Vinson & Elkins L.L.P.

[57] ABSTRACT

An electronic medical record system stores data about patient encounters arising from a content generator in free-form text. A header for each encounter record also uses text to store context information for each encounter record. Each header comprises a plurality of attributes embodied as a field descriptor and a value, bound together as a text object. By binding the field descriptors to the values, each encounter record is complete in itself, without reference to database keys, thereby providing a self-validating record storage system.

25 Claims, 6 Drawing Sheets

```
          @$N         MRN:  2222222
          @$p        Name:  Smith, Jane                    SSN:  222-22-2222
          @$1     Address:  2222 Short Trail               DOB:  09/15/55
          @$2     Address:  Salado, TX   22222             Sex:  F %$p  Encounter Purpose:  Personal Health Care    Date:  03/19/92
          %$e     Encounter Type:  Provider Care           Time:  03:30 pm
          %$n           Location:  Scott & White Clinic
          %$d         Department:  Psychiatry/Psychology
          %$o           Division:  Other
          %$i    Hospital Status:  OutPatient              ID:  0229
          %$1     First Provider:  Dr. Burke
          %$a         Speciality:  Psychiatry              ID:  NULL
          %$2    Second Provider:  NULL
          %$b         Speciality:  NULL              Reimburse:  HMO
          %$v    Type of Service:  obs
          %$c   Date Transcribed:  03/19/92     Date Dictated:  03/19/92

%$s        Date Signed:  NULL           Time Signed:  NULL
          %$h          Signature:  NULL %$x   CPT: NULL
          %$q   ICD9: NULL !$t   DICTATION:

$    Psychiatry/Psyc   03/19/92    Dr. Burke    Psychiatry    obs

SCOTT AND WHITE
                              PSYCHIATRY CLINIC NOTE

PATIENT NAME:  SMITH, JANE                MRN:  2222222
          DATE:  03/19/92
```

The patient reported that she has been sleeping better since discontinuing Zoloft, which had interfered with her sleep the last few nights of last week. She noted some improvement on the Zoloft, especially that she felt calmer and did not get into arguments so much. She said that her husband and salesmen at her store had also noticed the improvement. She would like to continue to find a way to have more piece of mind, but would not want to take any additional medication, such as a sleeping pill, to help with insomnia caused by Zoloft at this time. Her daughter has been free of seizures for the past four weeks, and she is hoping for a great deal of reassurance about her daughter's condition. The daughter has been controlled on Dilantin. In addition, the patient reports that she needs to undergo another gynecologic examination, which has been traumatic for her in

She apparently did have a therapeutic response to Zoloft but the problems with insomnia made it impossible for her to continue. We have discussed a possible trial of Paroxetine, which should have similar effects and maybe better tolerated. In addition, I have offered her Ativan 1 mg to take before examination scheduled with Dr. Pliego. Her husband will drive that day and will be with her throughout the time of the examination.

DIAGNOSIS:
1. Major depression, recurrent, moderate severity
2. Generalized anxiety disorder PLAN:
1. Begin trial of Paroxetine 10 mg (1/2 tablet) every day
2. Ativan 1 mg — prescription given, to be taken 30 minutes before pelvic examination
3. Return to clinic in three weeks.

Jack D. Burke, Jr. M.D./ tal
dd: 03/19/92      dt: 03/22/92
JOB #: 05423
RETURN FOR SIGNATURE

ELECTRONIC MEDICAL RECORD USING TEXT DATABASE

RELATED APPLICATIONS

This application is a continuation of application Ser. No. 08/354,446, filed as PCT/JP93/01676 Nov. 16, 1993, and entitled, "Electronic Medical Record Using Text Database," now abandoned, which is a continuation of application Ser. No. 08/084,282, filed Jun. 28, 1993, and entitled, "Electronic Medical Record Using Text Database," now abandoned.

TECHNICAL FIELD OF THE INVENTION

This invention relates in general to electronic medical record systems, and more particularly to an electronic medical record system using a text database to store medical encounter information.

BACKGROUND OF THE INVENTION

The art of medical record keeping has developed over centuries of medical practice to provide an accurate account of a patient's medical history. Record keeping in medical practice was developed to help physicians, and other healthcare providers, track and link individual "occurrences" between a patient and a healthcare provider. Each physician/patient encounter may result in a record including notes on the purpose of the visit, the results of physician's examination of the patient, and a record of any drugs prescribed by the physician. If, for example, the patient was referred to another clinic for additional testing, such as a blood analysis, this would form a separate medical encounter, which would also generate information for the medical record.

The accuracy of the medical record is of the utmost importance. The medical record describes the patient's medical history which may be of critical importance in providing future healthcare to the patient. Further, the medical record may also be used as a legal document.

Over the years, paper medical records have evolved from individual practitioners' informal journals to the current multi-author, medical/legal documents. These paper records serve as the information system on which modern medical practice is based. While the paper-based medical record system has functioned well over many decades of use, it has several shortcomings. First, while a paper-based record system can adequately support individual patient-physician encounters, it fails to serve as a source of pooled data for large-scale analysis. While the medical data in the paper-based records is substantial, the ability to adequately index, store and retrieve information from the paper-based mechanisms prevents efficient analysis of the data stored therein. Thus, paper medical records could be a rich source of information for generating new knowledge about patient care, if only their data could be accessed on a large scale. Second, each portion of the paper-based record is generated and kept at the site of the medical service. Hence, the total record is fragmented among many sites. Consequently, access by off-site physicians is less than optimal. The inability to access a complete medical record in a short period of time presents problems both for individual care and group care of patients.

Because of the shortcomings of the paper-based record, the electronic medical record (or "EMR") has been investigated for a number of years. An electronic medical record may be stored and retrieved electronically through a computer. The Institute of Medicine of the National Academy of Sciences performed a long-term study on improving patient records. This study was memorialized in "The Computer-Based Patient Record: An Essential Technology for Healthcare", National Academy Press, 1991. The committee concluded that the EMR was essential in improving information management capabilities in support of increasing uses and demands of patient data, both for improving the quality of healthcare and for managing its costs.

In today's practice environment, the inability of healthcare providers, administrators, researchers and governmental agencies to rapidly access and/or extract information from paper-based medical records represents a serious limitation with significant scientific and economic ramifications. Electronic medical record systems are expected to improve healthcare delivery by enhancing case management capabilities, and by leading to clinical practice research databases that provide valuable information on patient outcomes and clinic effectiveness.

Despite more than two decades of interest, however, development of a robust, fully-functioning electronic record system capable of supporting all components of the daily practice of medicine remains incomplete. Attempts to develop computer database architectures capable of storing and retrieving medical record information have failed to reconcile physicians' desires for maintaining a format of unstructured medical information with database requirements for highly structured data storage. Approaches have been based on the development of categorical data structures and descriptive vocabularies which require translation of medical information into highly-structured abstractions. This approach is problematic due to the enormous size of the overall translation task, the inability to accurately code all of the information contained within the free-text portion of the record, and the fact that normalizing data introduces additional abstraction, which may devalue its clinical worth.

Therefore, a need has arisen in the industry for an electronic medical record which provides efficient indexing, storage and retrieval of medical information without degrading the value of the information.

SUMMARY OF THE INVENTION

An electronic medical record system stores data about individual patient encounters arising from a content generator in free-form text. A header for each encounter-based record also uses text to store context information for that record. Each header comprises a plurality of attributes embodied as a field descriptor and a value, bound together as a text object. By binding the field descriptors to the values, each encounter record is complete in itself, without reference to database keys, thereby providing a self-validating record storage system.

The present invention provides significant advantages over other medical record systems. Importantly, the security of the medical data is enhanced over prior art systems. Because the attribute values and the attribute descriptors are bound together as a text object, and because the values are not location dependent, the data is self-validating. Thus, templates, keys, or other lookup means employed by relational database are never required to find or interpret the data. Additional attributes may be added without any restructuring process which may introduce errors into the system. Access of the content and context information in the EMR system by external systems is possible without secondary tables or keys.

BRIEF DESCRIPTION OF THE DRAWINGS

For a more complete understanding of the present invention, and the advantages thereof, reference is now made to the following descriptions taken in conjunction with the accompanying drawings, in which:

FIG. 3 illustrates an example of a record as formatted in the preferred embodiment of the invention;

DETAILED DESCRIPTION OF THE PREFERRED EMBODIMENTS

The present invention is best understood in reference to FIGS. 1–6 of the drawings.

The present invention seeks to provide an electronic medical record (EMR) system to enhance the value of information gathered from a provider-patient encounter. "Providers" include physicians, dentists, nurses and other medical personnel who have encounters with patients and are responsible for generating a portion of the patient's medical history as a result of the encounter. Common medical terminology refers to the complete collection of all data about a patient as comprising that patient's "record." In database terminology, a "record" refers to a single element of a collection of information. A collection of records is referred to as a database "file." In order to differentiate between the two uses of the term "record," elements of the textual database described herein will be referred to as "encounter records." The collection of all such encounter records pertaining to one such patient is referred to as his or her "medical record" or "chart."

In order to maximize the value of the information maintained by the EMR, it is important to facilitate both information entry, to ensure that the EMR can access all pertinent information, and information retrieval, to ensure that the information is accessible and that such retrieved information is accurately provided to the provider for proper interpretation. Further, the providers must have confidence that the information is accurate, secure, and fail-safe; otherwise, providers will be reluctant to rely upon the EMR for maintaining medical information needed in their practice. Further, the interface provided by the EMR system must accurately reflect the scope of the information being presented.

In the preferred embodiment, the EMR system is capable of receiving and transmitting information to a large number of offices, which may exist in multiple buildings at multiple sites. Data may be accessed from offices in the local area over a local area network and over a large area, even globally, over a wide area network.

Figure 1:
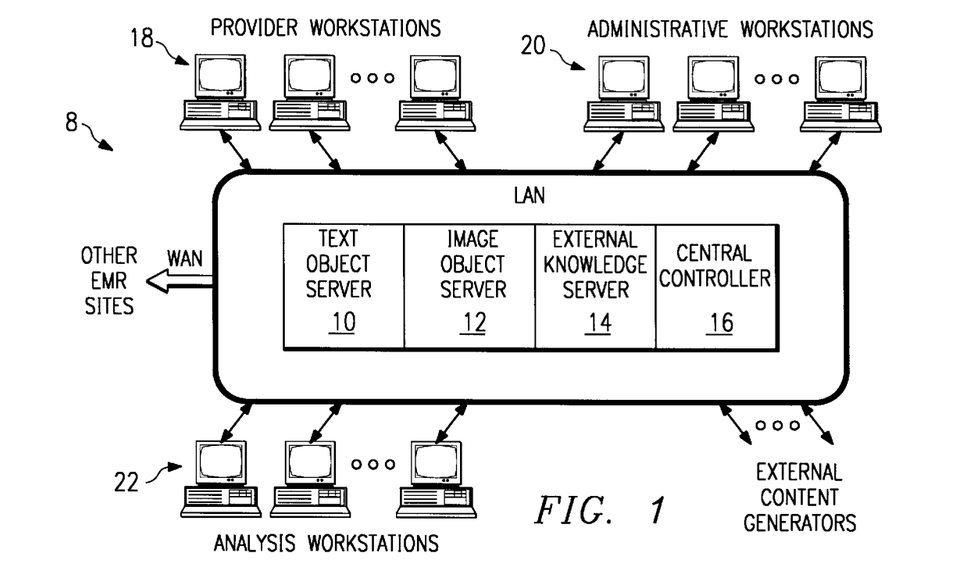
FIG. 1 illustrates a block diagram of the overall EMR network hardware.

FIG. 1 illustrates a block diagram of the overall EMR system 8. The network includes a local area network (LAN), typically in a client-server configuration. The LAN includes a plurality of servers, shown in FIG. 1 as a text object server 10, an image object server 12, an external object server 14 and a central controller 16. A plurality of workstations are coupled to the servers via the LAN. Specifically, provider's workstations 18, administrative workstations 20 and analysis workstations 22 are coupled to the servers. Additionally, the servers are coupled to other external content generators, such as laboratory systems, x-ray systems and business systems. Additional medical sites using the EMR system 8 may be linked via a wide area network (WAN).

Figure 2A:
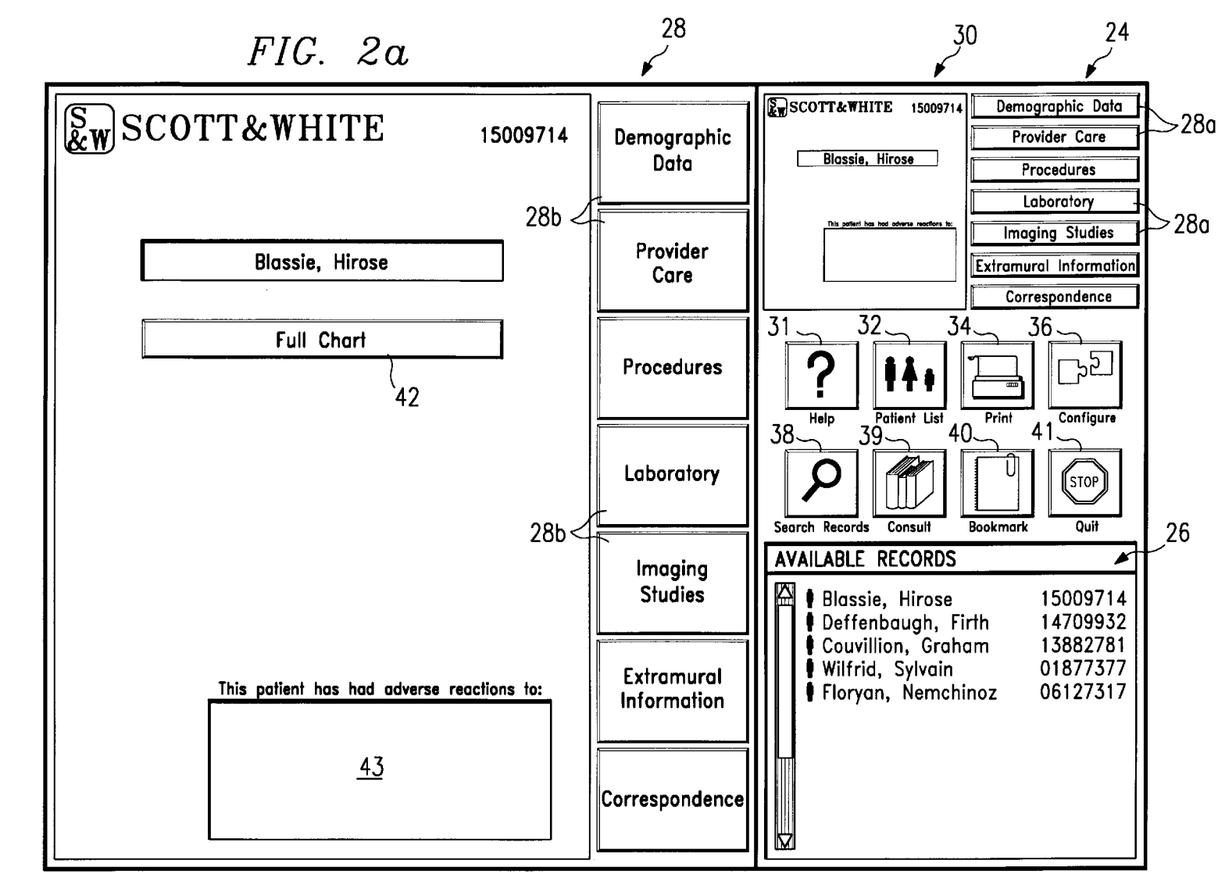
FIGS. 2a–b illustrate an interface 24 used at the provider's workstations 18 for processing patient information.
Figure 2B:
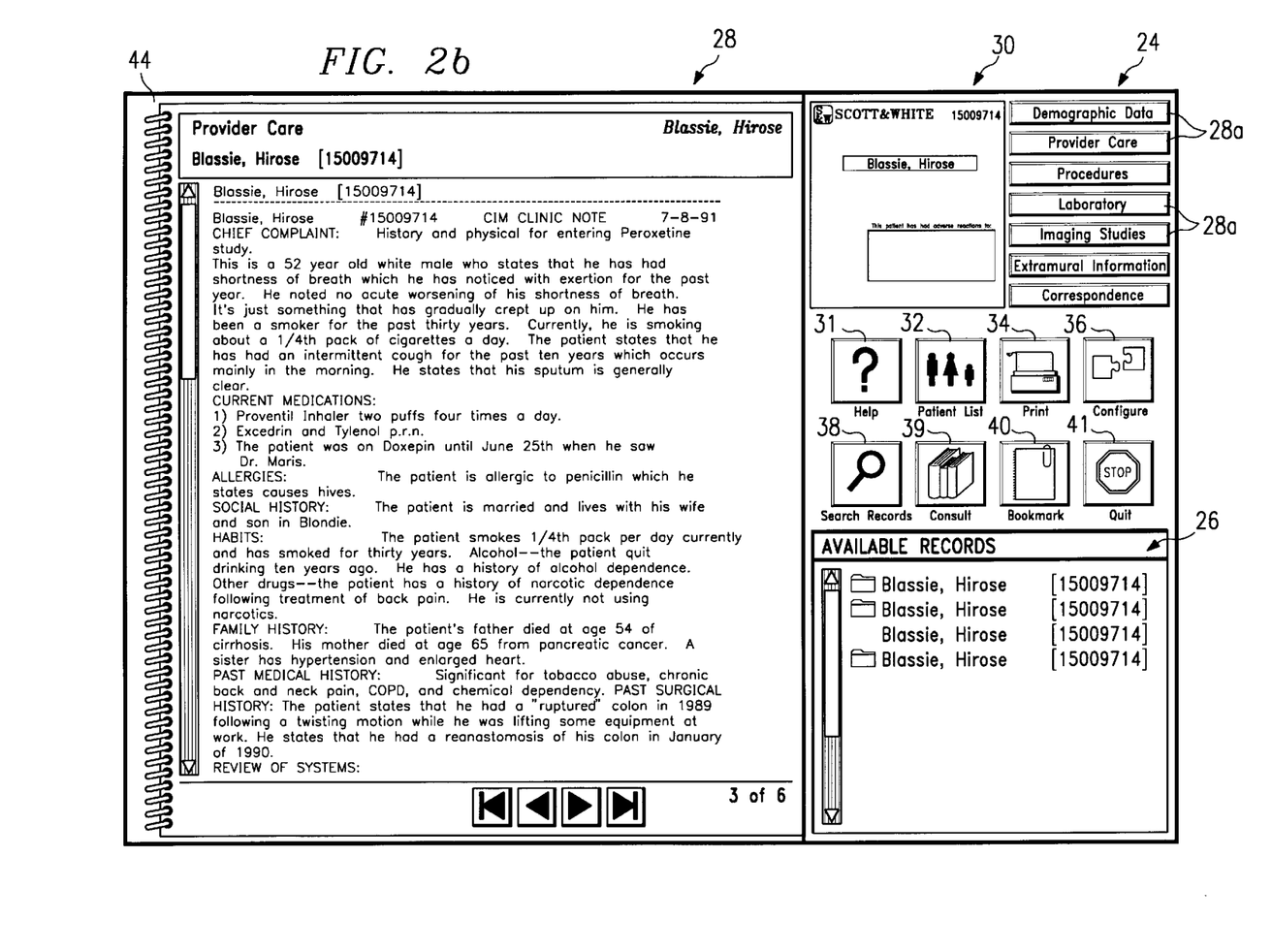

In the preferred embodiment, the LAN comprises a UNIX system or other open-architecture operating system. The workstations 18–22 are typically similar in terms of hardware, but differ in the software executed. The provider's workstations 18 provide software for retrieving and processing data from the servers 10–16 for use in patient care. An exemplary interface for this software is shown in FIGS. 2a–b. The administrative workstations include software for entering data resulting from provider-patient encounters. Other administrative functions, such as billing, may be supported by the software run on the administrative workstations. The analysis workstations 22 execute software for large-scale analysis of the data in the servers 10–16.

FIGS. 2a–b illustrate an interface 24 used at the provider's workstations 18 for processing patient information. The interface 24 is the gateway through which the providers gain access to collections of individual patient medical records. Along with retrieval of patient medical records, the interface 24 provides medical record display, sorting, manipulation and analysis.

The interface 24 allows the providers to view a medical record in an easily understood format. The format of the patient information displayed by the interface is based on the paper records that are normally associated with a patient, and is thus familiar to the user. The interface 24 combines the basic qualities of the paper record with the advantages of a complete electronic medical record. Replication of the paper record format allows the user to easily transfer already learned skills to the electronic presentation.

The Available Documents window 26 displays different information depending upon the mode of the interface 24. In the mode shown in FIG. 2a, the Available Documents window 26 displays a list of patients to be seen by the provider for that day. Each patient is listed by name and a unique patient identification code (the medical record number or "MRN").

The Main window 28 displays medical record data for the selected patient. A patient may be selected from the Available Documents window 26 by double-clicking on the desired patient's name. The medical record shown in the Main window 28 depends upon the encounter type selected. The encounter type may be selected using an encounter type button 29a from the Folder window 30 or using an encounter type button 29b from the list of encounter types on the right side of the Main window 28. As shown in FIG. 2a, seven encounter types are provided in the preferred embodiment: (1) Demographic Data, (2) Provider Care, (3) Procedures, (4) Laboratory, (5) Imaging Studies, (6) Extramural Information, and (7) Correspondence. Demographic Data includes the data normally supplied by the patient, such as name, address, sex, phone numbers and so on. Provider Care is the default encounter type and includes the documents that the providers have dictated and transcribed. A Provider Care document contains administrative information, observation information, diagnosis information and plan information. The Procedure encounter type includes documentation of procedures performed on the patient. The Laboratory encounter type includes documentation of laboratory tests performed on the patient. The Imaging Studies encounter type includes image data such as x-rays, cardiovascular scans, ultrasound scans and so on. The Extramural encounter type includes encounter records from outside sources, for example from a health club or a pharmacy. The Correspondence encounter type includes correspondence between the patient and the patient's healthcare providers.

When a patient is selected, a list of the patient's encounter records for the selected encounter type appears in the Available Documents window (see FIG. 2b). By default, the most recent document for the selected encounter type is displayed in the Main window 28. Other documents can be displayed by clicking on the desired document title in the Available Documents window 26.

A number of command buttons are provided above the Available Documents window 26. A Help button 31 provides the user with on-line instructions on the operation of the system. A Patient List button 32 displays the patient list in the Available Documents window 26. A Print button 34 prints selected documents. A Configure button allows the user to configure certain aspects of the interface 20 to desired settings. A Search Records button 38 allows the provider to search the medical records using Boolean searches.

A Consult button 39 allows the provider to access on-line reference manuals, such as the Physician Desk Reference, ICD-9 Classifications, Practice Guidelines, Scientific American, and CPT codes. The references may be searched by keyword. The Bookmark button 40 allows the provider to place an electronic bookmark in the medical records to facilitate a return to that portion of the medical record. A Quit button 41 allows the provider to sign off of the system.

The interface provides the ability to request condensed folders. When a patient's folder is initially selected, the folder appears in the Main window 28 with a box 42 entitled "FULL CHART." Also, a list of adverse reactions is provided in box 43. By clicking on the FULL CHART box 42, the title changes to "CUSTOM CHART." When CUSTOM CHART is selected, a list of available index forms is provided to narrow the number of documents shown. For example, a custom chart could be provided to show only those documents originating from a designated provider.

As can be seen in FIG. 2b, when full chart is displayed, a spiral icon 44 is displayed to the left of the text. When less than the full chart is displayed, for any reason, the spiral icon 44 disappears to notify the provider that a partial medical record is being displayed.

The present invention uses a unique text-based system. Previous attempts to develop computer database architectures capable of storing and retrieving medical record information have failed to reconcile provider's desires for maintaining a format of unstructured medical information with database requirements for highly structured data storage. Previous approaches have been based on the development of categorical data structures and descriptive vocabularies that require translation of medical information into highly structured abstractions. Whenever an abstraction replaces the original raw data, valuable information may be lost, which devalues its clinical worth.

The present invention maintains the original free-text content generated from a provider-patient encounter. Hence, the electronic medical record of the present invention can duplicate the entire content which would be generated using a paper record system. This allows healthcare providers freedom and flexibility in recording events associated with patient care as they are observed.

In a paper medical record, the aggregate composition of the data is relatively unstructured, even though portions of the data may have a defined order or structure. Most users easily assimilate the unstructured information present in a paper medical record, provided that the medical record is of modest size. In contrast, difficulties arise when mapping unstructured medical data to current relational database systems. These difficulties are compounded as the number of encounter records in the database is expanded, even if the quantity of data present in a single encounter record is small. While high-level cognition usually is sufficient to manually extract information from a single unstructured encounter record, these skills become severely taxed when the number of encounter records, or size of individual encounter records, is increased. Constraints on the providers' ability to easily analyze aggregated data, to provide insightful longitudinal care, to determine therapeutic outcomes, and to identify new diseases, have far reaching implications.

The preferred embodiment uses an object-oriented database model to reconcile the need for free text with the need for categorical data structures when indexing, storing, analyzing and retrieving machine-readable representations of medical information. A very desirable feature of object-oriented database models is their ability to provide a high degree of conformity between the computerized data model and the user's model of real-world data. The object data model can provide this one-to-one correspondence by representing a real-world entity—including free text or graphical images—using a corresponding object in the database. Thus, an object-oriented data model avoids normalizing or abstracting medical record information in order to categorize it for processing. The model assigns operators, or attributes, to complex medical objects in order to index, store, analyze and retrieve objects from a computerized repository.

In the preferred embodiment of the present invention, TEXT MACHINE software from Alliance Technologies of Austin, Tex., is used to perform the text database functions. Other database systems may be equally suited to performing the needed tasks. The TEXT MACHINE software provides for tokenization of the text in the database. For example, "<PN:John Smith>" is a token which indicates that "John Smith" is a proper name. Any object in the text database, which would include words, groups of words, sentences and paragraphs, may be treated as objects. Text input into the database may be parsed in relation to a desired dictionary. Parsing will tokenize words in the text according to the dictionary (or dictionaries). For example, it may be desirable to parse all text from a patient-provider encounter such that all drug names are tokenized. Tokenization in this manner adds information to the text, without any abstraction which would skew or eliminate the original content. It should be noted that an object in the text database may have multiple nested tokens. For example, a drug name may be tokenized as a drug and under multiple classifications of drugs. The tokenization codes are not displayed to the provider.

FIG. 3 illustrates an example of an encounter record (without showing tokenization) as formatted in the preferred embodiment of the invention. The encounter record 50 comprises a header 52 and a body portion 54. The body portion 54 is free text; i.e., the database does not place any constraints on what may be entered into the body portion 54. For example, the text of the body portion 54 may be any length, and the database does not dictate any particular format for the body portion 54 (although certain formats may be enforced by local practice standards; for example, the encounter record shown in FIG. 3 shows headings for "Diagnosis" and "Plan" which are not enforced by the EMR system 8, but rather by local rules of procedure).

Because there are no constraints on the body portion 54, the text found therein may be identical to that which would be found in a corresponding paper record for the same encounter. In fact, the mechanism for generating the body portion may be identical to that typically used for a paper record system. Tapes dictated by the provider may be transcribed into ASCII format (or another universal format) and input directly into the encounter record. Thus, standard procedures need not be changed to accommodate the EMR system 8.

Because the entire transcription is transferred into the encounter record 50, the EMR system 8 retains all the information that would be found in a paper record system. Prior art systems which require abstraction of information, or limit the amount of information which may be entered, result in a loss of information.

Furthermore, in the preferred embodiment, the EMR system 8 can be used to enhance the information shown in the body portion 54. While not shown for purposes of illustration, the body portion may be tokenized as described above. Tokenization may enhance the information in many ways. For example, through the use of a parser, key words, such as medications, can be identified and classified. Thus, a patient's chart, or a group of patients' charts, may be searched for a certain class of medications, such as anti-depressants, which will locate each anti-depressant in the body portion 54, even though the medication was not identified as such in the original transcription. Further, all drugs listed in a certain manual, such as the Physician's Desk Reference, can be highlighted and linked to the text of the manual dealing with the medication. Consequently, when a provider selects a highlighted term from the body portion, a window with the associated information from the manual is placed on the screen.

The header 52 classifies the free-text body portion 54 using a number of attributes. The attributes used in the preferred embodiment are shown in Table 1. Importantly, these attributes may be changed as the EMR system evolves, without the need to restructure the database. In order to enhance the speed of searching, the text in the header 52 is not tokenized in the preferred embodiment.

TABLE I

Attributes

| | |
|---|---|
| System Logical Identity | Hospital Status |
| MRN - Medical Record Number | First Provider/Specialty/ID |
| Name | Second Provider/Specialty/ID |
| Address | Type of Service |
| Sex | Reimburse |
| Date of Birth/Age | CPT |
| SSN - Social Security Number | ICD-9 |
| Encounter Purpose | Attached Media Data |
| Encounter Type | Attached Relational Data |
| Location/Department/Division | Time of Creation - Date Transcribed/Date Dictated/Date Signed/Signature/Identity of Data Generator |

The header 52 is also textual. Formatting codes 56 are provided for placing information from the header 52 onto the screen. In the preferred embodiment, the header text is formal, i.e., the attributes in the header (although not the value of the attributes) are predefined. Importantly, each attribute descriptor, such as "MRN:", "Name:", and so on, is a text object which is immutably coupled to the associated value, such as "222222", "Smith, Jane" and "222 Short Trail". Thus, "Name:Smith, Jane" forms a text object which includes both a descriptor and a value. This aspect of the invention provides significant benefits over prior art relational database structures wherein the field descriptor is associated to values only through keys which are associated with the database. If a key in a relational database is corrupted, the association between fields and values can be irretrievably lost. Also, in the present invention, additional attributes could be added (or existing attributes removed) to the header 52 without restructuring the database. In a relational database, any change in the structure of the database necessitates a restructure process. The restructuring process of a relational database can introduce errors leading to irretrievable data loss.

By using text to hold the attribute descriptors and values, future systems can easily access data from the EMR system 8 shown herein by importing the text (in ASCII format, in the preferred embodiment) and retrieving the appropriate values. No information on the structure of the database is needed to effect such a transfer, because each header is complete with both the field descriptors and the values associated with the descriptors.

Some of the header values shown in FIG. 3 are listed as "NULL." A NULL indicates that the information could not be supplied. For example, if only one healthcare provider was involved in the encounter, the fields associated with the second provider will be NULL. This distinguishes the value from a field in which the data was simply not provided, because the NULL value indicates that the attribute was considered and that no answer could be supplied. On the other hand, a blank merely indicates that no answer was supplied, without specifying that the answer could not be supplied.

Whenever possible, the values from external sources, specifically from an appointment scheduling system, are imported into the header. The mechanics for importing data from an external source is to receive ASCII text from the external source's report generation facilities. Importing information electronically from an external source allows the EMR system 8 to take advantage of the validation mechanisms of the external source. For example, an appointment scheduler will maintain a database of existing patient information based on the MRN. By using scheduler's validation mechanism, the EMR system 8 does not need to check each entry relating to patient demographic data for consistency with previous encounter records for a given patient. Accordingly, the complexity of the system is reduced.

Certain attributes must be selected from a predetermined list. For example, the Encounter Purpose attribute could be chosen from a list of "personal health care", "research", "employment", "legal" or other predetermined values. The Encounter Type attribute could be chosen from a list of "provider care", "lab", "imaging studies", "procedures", "demographic data" or other predetermined values.

The Attached Media Data and Attached Relational Data attributes appear in the header only if there is a corresponding object to be attached to the encounter record. For example, if an x-ray was generated as part of the encounter, the Attached Media Data attribute fields would be present in the header which described the type of media (for example, whether the media comprised graphics or video) and the location of the image. Similarly, the EMR system 8 can link to a relational database and display relational database data as part of the patient's chart. The Attached Media Data attribute fields would identify the type of database and the location of the database.

Figure 4:
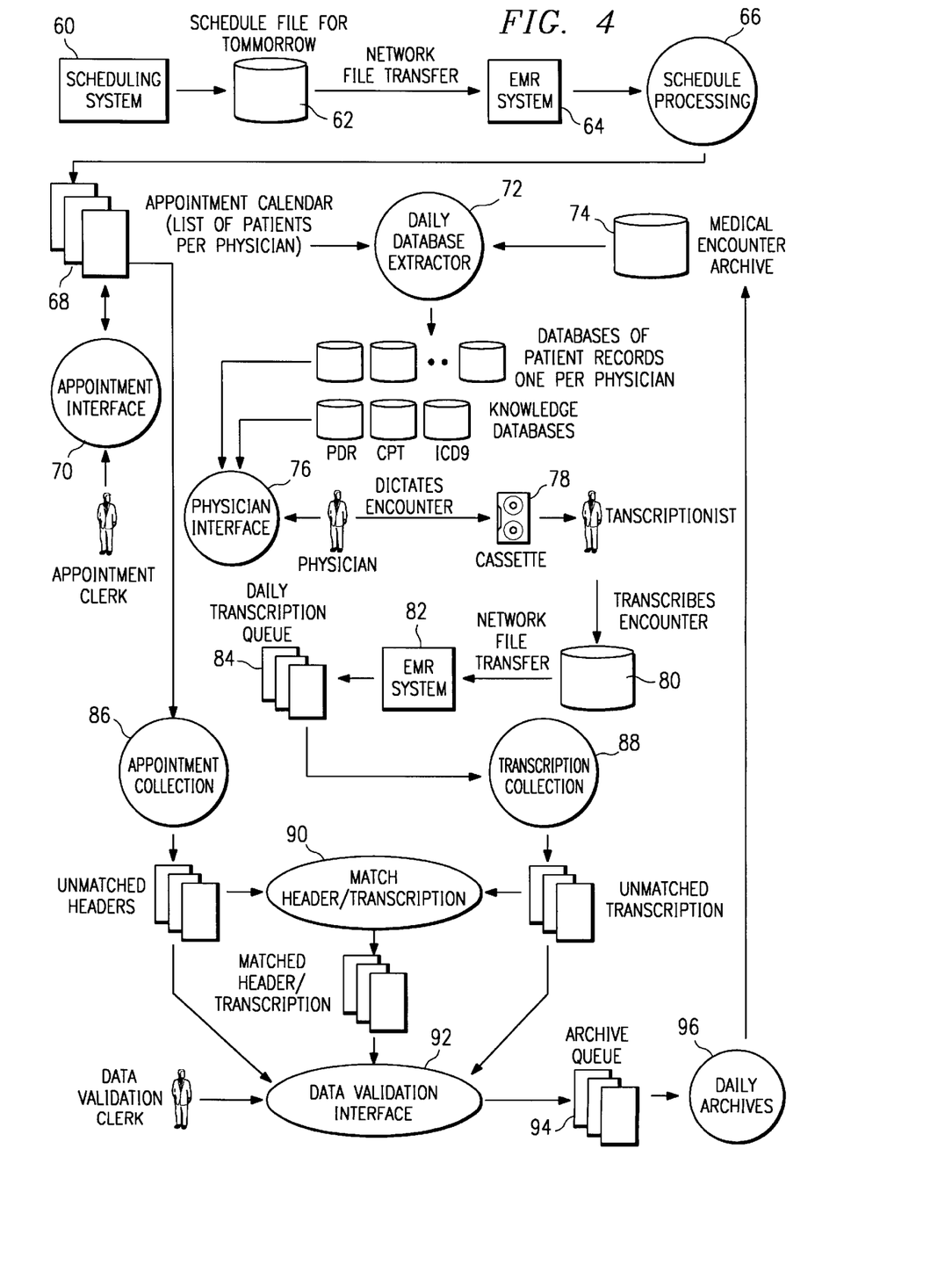
FIG. 4 illustrates a diagram describing creation of a record for the EMR system.

FIG. 4 illustrates a diagram describing creation of an encounter record for the EMR system 8. In block 60, information is entered into the scheduling system (separate from the EMR system 8) and stored in the mass storage 62.

The EMR system 8 retrieves data from the mass storage in block 64 and processes the scheduling information in block 66 to generate "shells" 68 for each anticipated encounter. The shell of the encounter record includes the attribute field names without values. Some values may be supplied by the information from the scheduling system and others may be supplied by the appointment clerk through the appointment interface 70 (either before or after the encounter).

In block 72, the partially filled shells are provided to the daily database extractor 74 to retrieve the encounter records from the textual database 74 for the patients to be seen that day, so that a chart can be formed for each patient. Individual databases are generated for each provider, each database comprising the charts for the patients to be seen that day. Through the provider interface, shown as block 76 and described in connection with FIGS. 2a–b, the provider has access to the patients' charts, and the encounters take place. After the encounter, the provider dictates the notes from the encounter in block 78, which are subsequently transcribed and stored (typically on the hospital's mainframe computer) in block 80. The EMR system 8 retrieves the transcribed dictation in block 82 and places the transferred files in a transcription queue 84. The headers and transcriptions (which form the body of the encounter record) are collected in blocks 86 and 88 respectively and associated headers and bodies are brought together to form a unified encounter record in block 90. The encounter records are validated in block 92 to ensure all necessary data has been entered and stored in an archive queue 94. At this point, the information in the encounter records (both the header and the body) may be revised by the provider. Also at this point, the archived encounter records are available as part of the patients' charts as shown in block 96, although they will be marked as non-final encounter records. This allows the information from an encounter to be readily available for a subsequent encounter.

Once an encounter record is "signed", it is posted to the text database. An encounter record may be signed in any of a number of ways. For example, a provider may sign an encounter record by supplying a one- or two-level password. After signing, the encounter record is complete and its contents cannot be changed. As part of the posting process, the body of the text is tokenized to enhance, but not alter, the text of the body. The complete encounter record, including the header and the body, is stored in the text database. Also, the header of the encounter record is separately stored in a master cataloguer, which is a file which holds the headers for each encounter record for verification purposes, described below.

Thus, as described above, the EMR system 8 receives "content", i.e., the output of the transcription system (or an imaging device), and adds "context", i.e., the attributes which reveal the environment in which the content was generated. Both the content and the context are in text form. For each encounter record, the EMR system 8 binds the content and the context together.

While the encounter records cannot be changed after posting the data to the text database, in one embodiment of the present invention, context information may be added to the encounter records after posting. For example, standards for certain test results may change over the years. To adjust the results to a new norm, information related to the lab results in pre-existing encounter records may be added. Whenever information is added to an encounter record, it is individually marked as added data, so as not to alter the original information. When viewing an encounter record to which information has been added, the provider is notified of the existence of the added information.

Figure 5:
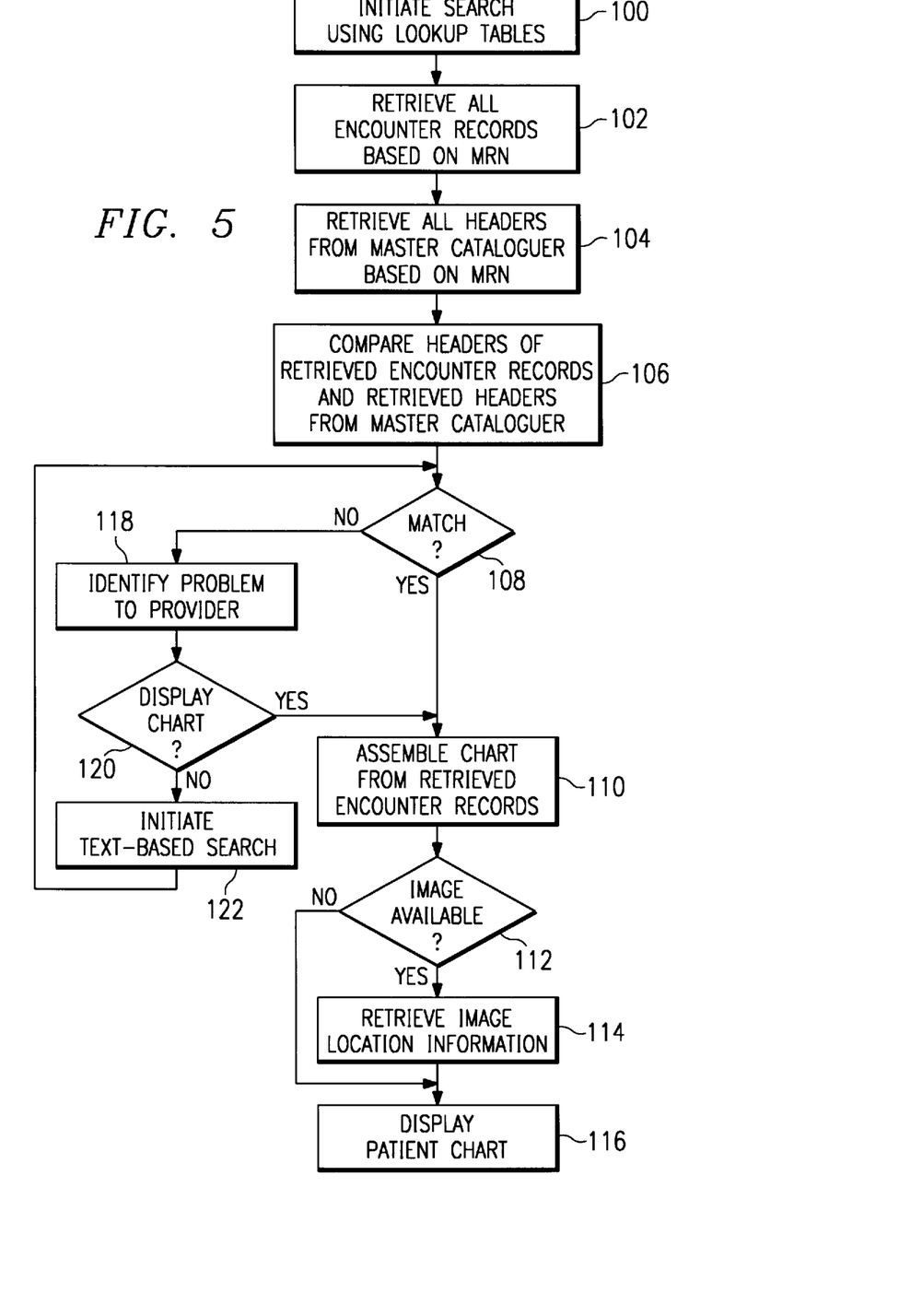
FIG. 5 illustrates a flow chart describing the chart assembly process.

FIG. 5 illustrates a flow chart describing the chart assembly process in greater detail. In block 100, a search is initiated for a patient's chart. Typically, the chart is requested using the patient's MRN as the search criteria. Based on the MRN, a lookup table is referenced to find the locations of the encounter records having the specified MRN. These encounter records are retrieved in block 102. In block 102, header information is retrieved from the master cataloguer for the specified MRN.

In block 106, the header information from the master cataloguer (block 104) is compared to the header information from the encounter records retrieved from the text server (block 102). In the preferred embodiment, the MRN and name values are compared for respective headers, although the comparison could include all attribute values in the respective headers.

If, in decision block 108, the headers of each of the retrieved encounter records match corresponding headers from the master cataloguer, then the encounter records are assembled into a chart in block 110. By default, the encounter records are assembled in reverse chronological order. If an image is available for one or more of the encounter records in decision block 112, then the information for retrieving the image from the image server 12 is retrieved in block 114, although the image itself is not retrieved until requested by the provider. In block 116, the chart is presented to the provider.

If, in decision block 108, a mismatch between the headers of the retrieved encounter records and the headers from the master cataloguer is detected, then the problem is identified to the provider in block 118. The provider has the option to display the chart as retrieved, perform extended searches of the text database, or not display the chart at all (not shown). If the provider chooses to display the chart as retrieved, for example if a single encounter record was missing, then the chart is assembled in block 110 as previously discussed. If additional searching is requested, then a text search is initiated which is capable of searching the text database without reference to the aforementioned look-up table, which may be the source of the problem. In the preferred embodiment, the extended search can use either predefined search algorithms or artificial intelligence to determine the best search based on the identified problem. For example, if a single encounter record was missing (which would be detected if a header from the master cataloguer did not have a corresponding header from the retrieved encounter records), then the text database may be searched for headers having the same name value as the unmatched header from the master cataloguer. The search could be further narrowed by the date of the appointment, as found in the unmatched header from the master cataloguer. Different searches may be tried under control of the provider until the encounter records for an acceptable chart is reached. Although it is not expected that errors in retrieving encounter records will occur often, the ability to search the headers as text without need for a lookup table or index key is an important strength of the present invention.

Figure 6:
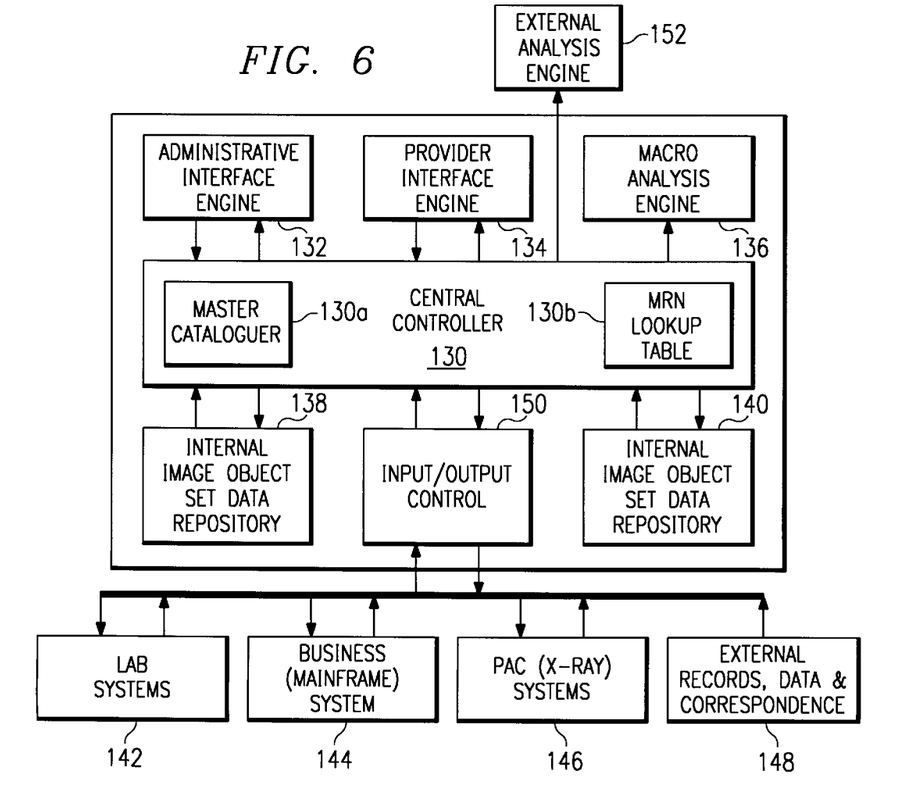
FIG. 6 illustrates a functional block diagram of the EMR system.

FIG. 6 illustrates a functional block diagram of the EMR system 8. The central controller logic 130 includes the master cataloguer 130a and the look-up tables 130b along with the text database software. The central controller logic 130 interfaces with the administrative interface engine 132 (on the administrative workstations 20), the provider interface engine 134 (on the provider workstations 18), and the macro analysis engine 136 (on the analysis workstations 22). The central controller logic 130 further interfaces with the internal text object set repository 138 (on the text object server 10), the internal image object set data repository 140 (on the image object server 12) and with external devices, such as lab systems 142, business systems 144, x-ray systems 146 and other external encounter records, data and correspondence devices 148 (for extramural data), through input/output control 150 (on the external knowledge server 14). Further, external systems 152 may request data from the central controller logic 130.

In operation, the engines 132–136 are programs operating on the respective workstation which interface with the central controller logic 130 to create, store and retrieve the medical records. The objects from which the medical records are comprised are stored and retrieved in the internal text and internal image object set data repositories 138 and 140. Data from external sources is transferred from the external source through the input/output control 150 to the appropriate data repository via the central control logic 130.

The present invention provides significant advantages over other medical record systems. Importantly, the persistence (stability) of the medical data is enhanced over prior art systems. Because the attribute values and the attribute descriptors are bound together as a text object, and because the values are not location dependent, the data is self-validating. Thus, templates, keys, or other lookup means employed by relational database are never required to find or interpret the data. Additional attributes may be added without any restructuring process which may introduce errors into the system.

Although the Detailed Description of the invention has been directed to certain exemplary embodiments, various modifications of these embodiments, as well as alternative embodiments, will be suggested to those skilled in the art. For example, alternative embodiments could use different sets of attributes or different manners of formatting the header data.

The invention encompasses any modifications or alternative embodiments that fall within the scope of the claims.

What is claimed is:

1. A method of maintaining electronic medical records, comprising the steps of:
    receiving output about individual patient encounters from a content generator;
    generating context information related to the output of the content generator in a free form text output;
    storing context information for each individual patient encounter in a textual database comprising a plurality of encounter records, said storing step comprising:
        forming a textual header for an encounter record in the database corresponding to the individual patient encounter, said textual header having a variable plurality of descriptors and associated values bound together as a string of text; and
        appending the textual header to the generated context information to form the encounter record, wherein a text object is formed; and
        responsive to a user command, displaying information from said textual database on a display.

2. The method of claim 1 wherein said generating step comprises the step of generating tokenized text related to the output of the content generator.

3. The method of claim 1 wherein said generating step comprises the step of generating textual context information related to the output of the content generator and indicating whether an image is associated with textual context information.

4. The method of claim 1 wherein said generating step comprises the step of generating textual context information related to the output of the content generator and indicating whether a relational database object is associated with textual context information.

5. A method of maintaining electronic medical records, comprising the steps of:
    receiving output about individual patient encounters from a content generator;
    generating context information related to the output of the content generator;
    storing context information for each individual patient encounter in a textual database comprising a plurality of encounter records, said storing step comprising:
        forming a textual header for an encounter record in the textual database corresponding to the individual patient encounter, said textual header having a plurality of descriptors and associated values bound together as a string of text;
        appending the textual header to the generated context information to form the encounter record in the textual database, wherein a text object is formed; and
        storing the headers for each encounter record in a header database separate from said textual database; and
        responsive to a command from a user, displaying information from said textual database on a display.

6. The method of claim 5 and further comprising the steps of:
    searching the textual database to retrieve encounter records with headers having a predefined context value;
    searching the header database to retrieve headers having said predefined context value; and
    comparing the retrieved headers from the header database with headers of the retrieved encounter records.

7. The method of claim 6 and further comprising the step of forming a chart from the retrieved encounter records.

8. The method of claim 7 and further comprising the step of notifying the user if the retrieved headers from the header database do not match the headers of the retrieved encounter records.

9. The method of claim 8 wherein, if the retrieved headers from the header database do not match the headers of the retrieved encounter records, the user may selectively display a chart of the retrieved encounter records.

10. The method of claim 8 wherein, if the retrieved headers do not match the headers of the retrieved encounter records, the user may selectively perform a text search of the encounter records to locate one or more encounter records corresponding to retrieved headers which were not retrieved from the search of the text database.

11. An electronic medical record system comprising:
    one or more content generators;
    a plurality of workstations for storing and retrieving information related to electronic medical records; and
    a central controller coupled to said workstations and said content generators for:
        receiving output about individual patient encounters from a content generator;
        generating context information related to the output of the content generator;
        storing context information for each individual patient encounter in an encounter record in a textual database comprising a plurality of encounter records, said storing step comprising:
            forming a textual header for an encounter record in the database corresponding to the individual patient encounter, said textual header having a plurality of descriptors and associated values bound together as a string of text; and appending the textual header to the generated context information to form the encounter record, wherein a text object is formed; and responsive to a user command, displaying information from said textual database on a display.

12. The electronic medical record system of claim 11 wherein the content generators include a transcription system.

13. The electronic medical record system of claim 11 wherein one or more of said workstations include an interface for retrieving and displaying the encounter records responsive to inputs from a user.

14. The electronic medical record system of claim 11 wherein said workstations, content generators and central controller are coupled via a local area network.

15. The electronic medical record system of claim 14 and further comprising a wide area network coupled to the local area network.

16. The electronic medical record system of claim 11 wherein said central controller tokenizes the output of the content generator.

17. The electronic medical record system of claim 11 wherein said central controller stores the output of said one content generator in the encounter record as free-form text.

18. The electronic medical record system of claim 11 wherein said central controller stores said bound descriptors and associated values in a predefined header text format.

19. The electronic medical record system of claim 11 wherein said central controller stores context information in said header indicating whether an image object is associated with the encounter record.

20. The electronic medical record system of claim 11 wherein said central controller stores context information in said header indicating whether an relational database object is associated with the encounter record.

21. The electronic medical record system of claim 11 wherein said central controller includes a header database for storing the header information associated with each encounter record.

22. The electronic medical record system of claim 11 wherein said central controller searches the textual database for selected encounter records to form a chart.

23. The electronic medical record system of claim 22 wherein said central controller searches the textual database by:

searching the textual database to retrieve encounter records with headers having a predefined context value;

searching the header database to retrieve headers having said predefined context value; and comparing the retrieved headers from the header database with the headers of the retrieved encounter records.

24. The electronic medical record system of claim 23 wherein said central controller includes a lookup table for storing encounter record location information.

25. The electronic medical record of claim 24 wherein said central controller is operable to search the textual database without reference to the lookup table.

* * * * *